United States Patent [19]

Lubisch et al.

[11] Patent Number: 5,118,682

[45] Date of Patent: Jun. 2, 1992

[54] P-HYDROXY PHENONE DERIVATIVES AND THE USE THEREOF

[75] Inventors: Wilfried Lubisch, Mannheim; Manfred Raschack, Weisenheim am Sand; Gerda von Philipsborn, Weinheim, all of Fed. Rep. of Germany

[73] Assignee: BASF Aktiengesellschaft, Ludwigshafen, Fed. Rep. of Germany

[21] Appl. No.: 378,966

[22] Filed: Jul. 12, 1989

[30] Foreign Application Priority Data

Jul. 28, 1988 [DE] Fed. Rep. of Germany ....... 3825559

[51] Int. Cl.$^5$ .................. A61K 31/40; A61K 31/435; C07D 265/30; C07D 211/20
[52] U.S. Cl. ................................ 514/239.2; 514/317; 514/428; 544/175; 546/237; 548/571
[58] Field of Search ............ 548/571; 514/428, 239.2, 514/317; 544/175; 546/237

[56] References Cited

U.S. PATENT DOCUMENTS

| | | | |
|---|---|---|---|
| 3,964,940 | 6/1976 | Hart et al. | 548/141 |
| 4,140,770 | 2/1979 | Repplinger et al. | 548/141 |
| 4,407,233 | 10/1968 | Packman | 548/141 |

FOREIGN PATENT DOCUMENTS

| | | |
|---|---|---|
| 1174311 | 7/1964 | Fed. Rep. of Germany . |
| 2062129 | 6/1971 | Fed. Rep. of Germany . |
| 2616484 | 10/1977 | Fed. Rep. of Germany . |
| 5003M | 5/1987 | France . |
| 1022648 | 3/1966 | United Kingdom . |

OTHER PUBLICATIONS

Circulation (An Official Journal of the American Hear Association), vol. 68 Jul.-Dec. 1983, pp. 87-94.
American Heart Journal, vol. 109 No. 4, Apr. 1985, pp. 943-958.
Journal of Clinical Pharmacology, vol. 27, Jan. 1987 pp. 707-708.
Archiv Der Pharmazie (Und Berichte Der Deutschen Pharmazeutischen Gesellschaft) 1966, p. 299.

*Primary Examiner*—Johann Richter
*Attorney, Agent, or Firm*—Oblon, Spivak, McClelland, Maier & Neustadt

[57] ABSTRACT p-Hydroxy phenone derivatives of the general formula I

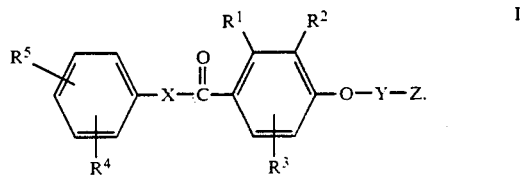

where
$R^1$, $R^2$ and $R^3$ are identical or different and are methyl, chlorine, bromine and hydrogen, but $R^1$, $R^2$ and $R^3$ are not all H,
$R^4$ and $R^5$ are identical or different and are H, $C_1$-$C_4$-alkyl, or $OR^6$, but $R^4$ and $R^5$ are not both H,
X is a —CH=CH—, —CH$_2$CH$_2$ or —CH$_2$— bridge,
Y is a straight-chain or branched, saturated or unsaturated $C_1$-$C_4$ bridge, and
Z is $NR^6R^7$, where $R^6$ and $R^7$ are, independently of one another, hydrogen or $C_{1-4}$-alkyl, or Z is a 5- or 6-membered ring with a nitrogen atom in the 1 position and, where appropriate, additionally a second N atom or an O or S atom, the second N atom being substituted by $R^7$, as well as the physiologically tolerated salts thereof, are used to prepare drugs antiarrhythmic of Vaughan-Williams class III.

7 Claims, No Drawings

P-HYDROXY PHENONE DERIVATIVES AND THE USE THEREOF

The invention relates to new p-hydroxy phenone derivatives, to drugs containing them, and to the use thereof for the preparation of antiarrhythmics of Vaughan-Williams class III.

Antiarrhythmics can be classified according to Vaughan-Williams into 4 groups, as follows:
  I. sodium antagonists,
  II. adrenergic β-receptor blockers,
  III. potassium channel inhibitors,
  IV. calcium antagonists.

Antiarrhythmics of class III often exhibit the therapeutic advantage of acting against arrhythmias which are otherwise resistant to therapy, especially reentry arrhythmias. This has been reported both for amiodarone (Circulation 68 (1) (1983), 88–94) and for D-sotalol (Am. Heart J. 109 (1985), 949-958; J. Clin. Pharmacol. 27 (9) (1987), 708.

p-Hydroxy phenone derivatives have been reported to have a variety of physiological actions: as spasmolytics (DE 2,616,484, DE 1,174,311, Arch. Pharm. 1966, 299), antiulcer agents (JP-A2 52/078-858, JP-A2 52/078-856, JP-A2 51/100-050), amoebicides (FR 5003 M) and vaso-dilators (JP-B4 27177/65, GB 1,022,648, US 3,407,233, DE 2,062,129, JP-B4 40/06903, JP-B4 40/06904, JP B4 74/021125).

The novel p-hydroxy phenone derivatives according to the invention are, by contrast, surprisingly antiarrhythmics of class III.

The present invention relates to p-hydroxy phenone derivatives of the formula I

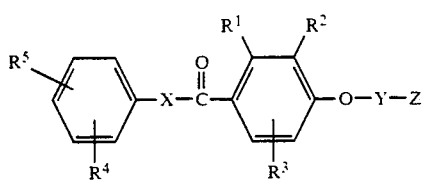

where
- $R^1$, $R^2$ and $R^3$ are identical or different and are methyl, chlorine, bromine and H, but $R^1$, $R^2$ and $R^3$ are not all H, $R^4$ and $R^5$ are identical or different and are H, $C_1-C_4$-alkyl, straight-chain or branched, or $OR^6$, but $R^4$ and $R^5$ are not both H,
- X is $-CH=CH-$, $-CH_2CH_2$ and $-CH_2-$,
- Y is a straight-chain or branched, saturated or unsaturated $C_1-C_4$ bridge, and
- Z is where $NR^5R^7$, where $R^5$ and $R^7$ are, independently of one another, hydrogen or $C_{1-4}$-alkyl, or Z is a 5- or 6-membered ring with a nitrogen atom in the 1 position and, where appropriate, additionally a second N atom or an O or S atom, the second N atom being substituted by $R^7$, as well as the physiologically tolerated salts thereof.

The compounds according to the invention can be prepared, for example, as shown in reaction schemes A and B which follow:

Reaction scheme A:

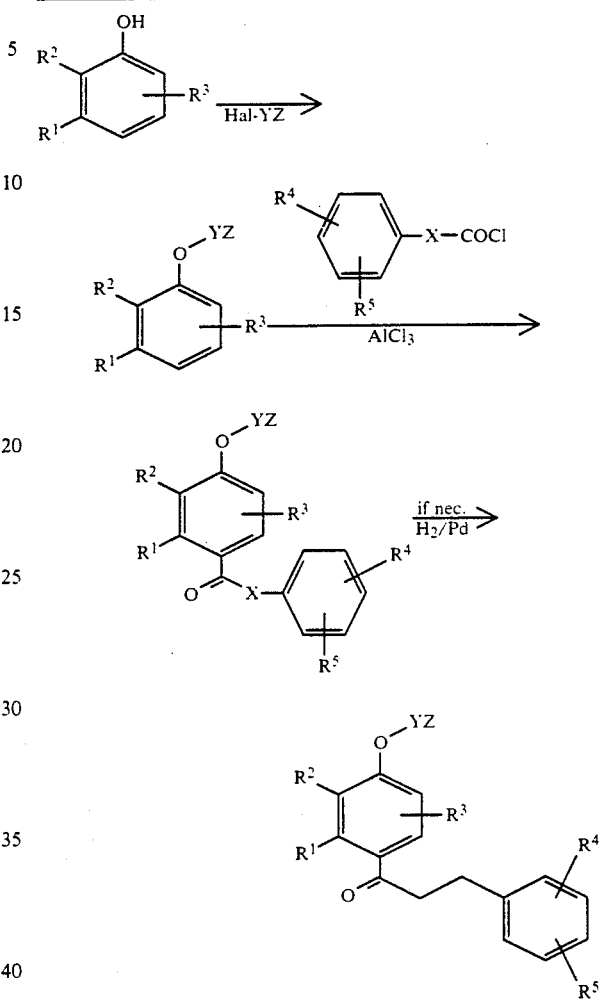

The phenol is alkylated in a conventional manner with a haloalkylamine, after which a Friedel-Crafts reaction with an acid chloride, for example of the structure

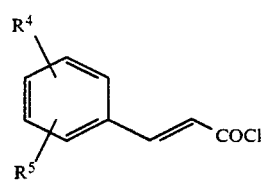

results in the chalcone of the formula I, which is hydrogenated if necessary.

Reaction scheme B:

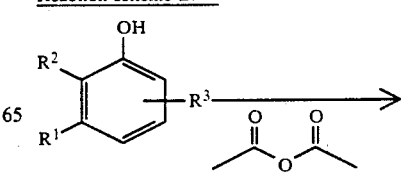

Reaction scheme B:

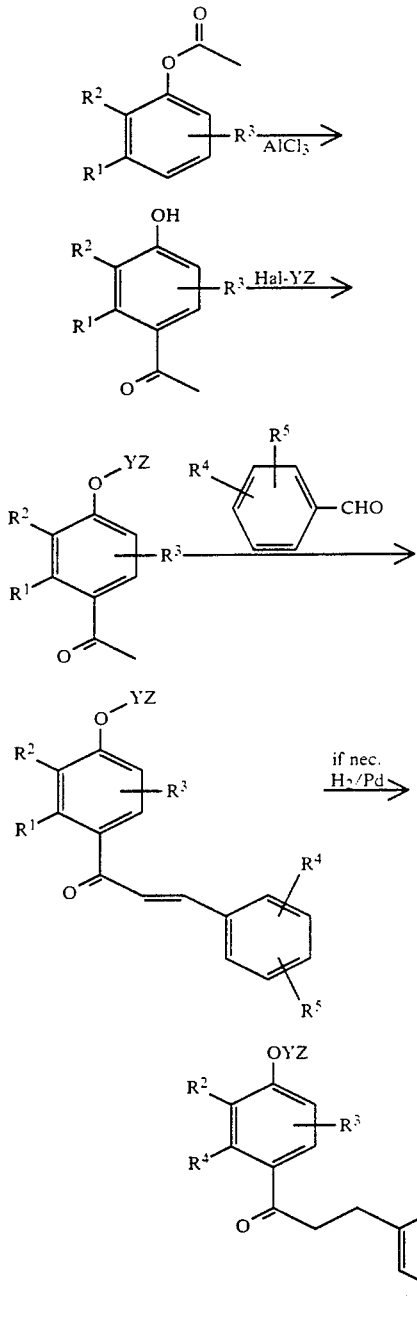

The phenol is esterified with acetic anhydride in a conventional manner. The Fries rearrangement in an AlCl₃ melt is followed by the phenol alkylation. The condensation with an aldehyde and the hydrogenation which may be desired are carried out by conventional methods described in Houben-Weyl, Methoden der organischen Chemie (Methods of Organic Chemistry).

The phenol alkylation and condensation steps in the reaction can also be carried out in the reverse sequence.

If necessary, the p-hydroxy phenone derivatives obtained in this way are converted into the addition salt of a physiologically tolerated acid. A compilation of conventional physiologically tolerated acids can be found in Fortschritte der Arzneimittelforschung (Advances in Drug Research) 1966, Birkhäuser Verlag, vol. 10, pages 244 to 285, Germany, Switzerland.

As a rule, the acid addition salts are obtained in a conventional manner by mixing the free base or solutions thereof with the appropriate acid or solutions thereof in an organic solvent, for example a lower alcohol such as methanol, ethanol or propanol, or a lower ketone such as acetone, methyl ethyl ketone or methyl isobutyl ketone, or an ether such as diethyl ether, tetrahydrofuran or dioxane. Mixtures of the said solvents can be used to improve crystallization. In addition, pharmaceutically acceptable aqueous solutions of acid addition compounds of the p-hydroxy phenone derivatives of the formula I can be prepared by dissolving the free bases in an aqueous solution of the acid.

The present invention also relates to therapeutic agents for topical and, especially, systemic administration, which contain a compound of the formula (I), besides conventional carriers and/or other pharmaceutical aids, as active substance, and to the use of a compound of the formula (I) for the preparation of a drug, in particular of an antiarrhythmic.

The novel compounds have, as is shown by the following experimental results, a good class III antiarrhythmic action:

The experimental animals are male and female Pirbright white guinea-pigs weighing from 300 to 500 g. They are anaesthetized with 1.5 g/kg urethane i.p. The substances are administered intravenously. The ECG conduction times and the heart rate are measured from a recording from extremity lead II. The measured variables are the QT and PQ intervals and the heart rate. 4 to 6 animals are used per dose. The criterion of a class III action is an increase in the QT interval compared with the values before administration of the substance. An increase in PQ and a large decrease in the heart rate serve as exclusion criteria. The ED 20 % is calculated from the linear relation between log dose (mg/kg) of the substance and the relative increase in the QT interval (in %).

TABLE 1

| | class III antiarrhythmic action in guinea-pigs after intravenous administration. | |
|---|---|---|
| Example No. | Increase in QT interval ED 20% [mg/kg] | Rel. action ED$_{20}$ (D-sotalol) ED$_{20}$ (example) |
| 1 | 0.74 | 4.9 |
| 2 | 0.76 | 4.7 |
| 3 | 0.65 | 5.5 |
| 4 | 0.89 | 4.0 |
| 10 | 1.31 | 2.7 |
| 12 | 0.74 | 4.9 |
| 13 | 0.67 | 5.4 |
| 15 | 1.5 | 2.4 |
| 17 | 1.69 | 2.1 |
| 18 | 1.5 | 2.4 |
| 20 | 0.73 | 4.9 |
| 24 | 0.95 | 3.8 |
| 25 | 0.79 | 4.6 |
| 27 | 1.2 | 3 |
| 32 | 1.62 | 2.2 |
| D-sotalol | 3.6 | 1 |

The substances according to the invention (Table 1) are more effective than the known class III antiarrhythmic D-sotalol in terms of increasing the QT interval.

The novel substances are therefore suitable for the treatment of arrhythmias otherwise resistant to therapy, in particular they eliminate ventricular tachycardias occuring after myocardial infarct and based on a reentry mechanism (Lit. Cardiac Arrhythmia, Ed. P. Brugada. H. J. J. Wellens, Futura Publishing Co., Mount Kisko, N.Y. 1987).

The therapeutic agents or compositions are prepared by mixing the active substance with the conventional liquid or solid carriers or diluents and the aids conventionally used in pharmaceutical technology, in accordance with the desired mode of administration and with the dosage suitable for the application.

The agents can be administered orally, parenterally or topically. Examples of compositions of this nature are tablets, film-coated tablets, sugar-coated tablets, capsules, pills, powders, solutions or suspensions, infusion or injection solutions as well as pastes, ointments, gels, creams, lotions, dusting powders, solutions or emulsions and sprays.

The therapeutic agents can contain the compounds to be used according to the invention in a concentration of from 0.0001 to 1 %, preferably 0.001 to 0.1 %, for local application and preferably in a single dose of from 10 to 500 mg for systemic administration and can be administered in one or more doses each day, depending on the nature and severity of the disease.

Examples of aids conventionally used in pharmaceutical technology are, for local application, alcohols such as ethanol, isopropanol, ethoxylated castor oil or ethoxylated hydrogenated castor oil, polyacrylic acid, glycerol monostearate, liquid paraffin, petrolatum, lanolin, polyethylene glycol, polypropylene glycol, stearate and ethoxylated fatty alcohol and, for systemic administration, lactose, propylene glycol and ethanol, starch, talc and polyvinylpyrrolidone. It is also possible to add to the products an antioxidant, for example tocopherol and butylated hydroxyanisole or butylated hydroxytoluene, or additives to improve the flavor, stabilizers, emulsifiers, bleaching agents etc. It is requisite that all the substances used in the preparation of pharmaceutical compositions are toxicologically innocuous and compatible with the active substances used.

EXAMPLE 1

3',5'-Dimethyl-4,-(2-(1-pyrrolidinyl)ethoxy)-2-methylchalcone tosylate 46.7 g (0.38 mol) of 2,6-dimethylphenol, 65.0 g (0.38 mol) of N-(2-chloroethyl)pyrrolidine hydrochloride, 210.1 g (1.52 mol) of potassium carbonate and 2 g of NaI in 300 ml of ethyl methyl ketone were refluxed for 48 h. The reaction mixture was concentrated under reduced pressure. The residue was partitioned between water and ether, the organic phase was separated off, washed with water and dried, and excess ethereal hydrogen chloride solution was added. The precipitated product was recrystallized from 10/1.ethyl acetate/isopropanol. 63 g of 2-(2,6-dimethylphenoxy)ethyl-N-pyrrolidine hydrochloride were obtained.

10.4 g (78.2 mmol) of anhydrous aluminum chloride were added in portions to 10 g (39.1 mmol) of 2-(2,6-dimethylphenoxy)ethyl-N-pyrrolidine hydrochloride and 8.5 g (46.9 mmol) of E-(2-methyl)cinnamoyl chloride which were dissolved in 100 ml of methylene chloride. The reaction mixture was then refluxed for 1 h and poured onto ice. The resulting solution was made alkaline, and the organic phase was separated off, washed with water and concentrated under reduced pressure. The residue was dissolved in a little hot acetone, and a hot equimolar solution of toluenesulfonic acid in acetone was added. Cooling resulted in 11 g of 3',5'-dimethyl-4'-(2-(1-pyrrolidinyl)ethoxy)-2-methylchalcone tosylate.

Melting point 169°-171° C.

The following were prepared in a manner similar to Example 1:

2. 3',5'-Dimethyl-4'-(2-(1-piperidinyl)ethoxy)-2-methylchalcone fumarate
Melting point 160°-163° C.
3. 4'-(2-Diethylaminoethoxy)-3',5'-dimethyl-2-methylchalcone fumarate
Melting point 128°-131° C.
4. 3',5'-Dimethyl-4'-(3-(1-pyrrolidinyl)propoxy)-2-methylchalcon fumarate
Melting point 144°-146° C.
5. 4'-(2-Di-n-butylaminoethoxy)-3'5'-dimethyl-2-methylchalcone semifumarate
Melting point 79° C.
6. 2',6'-Dimethyl-4'-(2-(1-pyrrolidinyl)ethoxy)-2-methylchalcone semifumarate
Melting point 146°-147° C.
7. 4'-(2-(1-Pyrrolidinyl)ethoxy-2',3',5'-trimethyl-2-methylchalcone fumarate
Melting point 125°-128° C.
8. 3',5'-Dimethyl-4'-(2-(1-pyrrolidinyl)ethoxy)-2-methyldeoxybenzoin oxalate
Melting point 194°-196° C.
9. 3',5'-Dimethyl-4'-(2-(1-pyrrolidinyl)ethoxy-4-methoxydeoxybenzoin oxalate
Melting point 150°-152° C.
10. 4'-(2-Diethylaminoethoxy)-3',5'-dimethyl-4-methoxydeoxybenzoin oil

EXAMPLE 11

4'-(2-Diethylaminoethoxy)-2',6'-dimethyl-2-methylchalcone fumarate 206.5 g (1.69 mol) of 3,5-dimethylphenol and 337.3 g (3.30 mol) of acetic anhydride were refluxed for 1 h and then stirred at RT overnight. The mixture was poured onto water and extracted with methylene chloride. The organic phase was washed with sodium hydroxide solution and water, dried and concentrated under reduced pres-sure. 286 g of 3,5-dimethylphenyl acetate were obtained.

206.7 g (1.55 mol) of anhydrous aluminum chloride were added in portions to 246.3 g (1.5 mol) of the above product. The mixture was heated at 110° C for about 30 min and left to cool. The glassy mass was dissolved in methylene chloride and poured onto ice/conc. HCl. The organic phase was separated off, washed with water, dried and concentrated under reduced pressure. The resulting residue was recrystallized from petroleum ether. 171 g of 2,6-dimethyl-4-hydroxyacetophenone were obtained.

45.15 g (0.275 mol) of the above product, 37.35 g (0.275 mol) of N-(2-chloroethyl)diethylamine, 75.9 g (0.55 mol) of potassium carbonate and 0.5 g of 18-crown-6 in 250 ml of ethyl methyl ketone were refluxed for 2 h. The precipitate was filtered off, and the filtrate was concentrated under reduced pressure. The product obtained in this way was suspended in sodium hydroxide solution and extracted with ether, which was subsequently washed with water, dried and concentrated under reduced pressure. The oil was taken up in hot isopropanol, and a hot equimolar solution of oxalic acid in isopropanol was added. Cooling resulted in 85 g of 4-(2-(N,N-diethylamino)-ethoxy)2,6-dimethyl acetophenone.

7.65 g (0.029 mol) of the basic amine of the above product and 6.98 g (0.058 mol) of o-tolualdehyde were dis-solved in 100 ml of methanol. Then 11.6 g of 50 % strength sodium hydroxide solution were added and the mixture was refluxed for 2 h and left to stir at RT overnight. The reaction mixture was concentrated under reduced pressure, diluted with water and extracted with methylene chloride. The organic phase was then washed with water, dried and concentrated under reduced pressure. The residue obtained in this way was dissolved in a little hot ethanol, and an equimolar ethanolic fumaric acid solution was added. 9.5 g of 4'-(2-(N,N-diethylamino)ethoxy)-2',6'-dimethyl-2-methylchalcone fumarate were obtained.

Melting point 132°–134° C.

The following were prepared in a manner similar to Example 11:

12. 3',5'-Dimethyl-4,-(2-(1-pyrrolidinyl)ethoxy)-2-ethylchalcone fumarate
 Melting point 138°–140° C.
13. 3',5'-Dimethyl-4'-(2-(1-pyrrolidinyl)ethoxy)-2-methoxychalcone fumarate
 Melting point 141°–145° C.
14. 3',5'-Dimethyl-4,-(2-(1-pyrrolidinyl)ethoxy)-3-methoxychalcone hydrochloride
 Melting point 169°–173° C.
15. 3',5'-Dimethyl-4'-(2-(1-pyrrolidinyl)ethoxy)-4-methoxy-2-methylchalcone oxalate
 Melting point 167° C.
16. 2',6'-Dimethyl-4'-(2-(1-piperidinyl)ethoxy)-2-methoxychalcone fumarate
 Melting point 127°–131° C.
17. 3',5'-Dimethyl-4'-(2-(1-piperidinyl)ethoxy)-2-methoxychalcone hydrochloride
 Melting point 201°–203° C.
18. 3',5'-Dimethyl-4'-(2-(1-morpholinyl)ethoxy)-2-ethylchalcone hydrochloride
 Melting point 193°–196° C.
19. 2',6'-Dimethyl-4,-(2-(1-pyrrolidinyl)ethoxy)-2-ethylchalcone hydrochloride
 Melting point 153°–155° C.
20. 3',5'-Dimethyl-4'-(2-(1-piperidinyl)ethoxy)-4-methoxy-2-methylchalcone fumarate
 Melting point 163°–166° C.

EXAMPLE 21

4'-(3-Diethylaminopropoxy)-2',6'-dimethyl-2-methylchalcone hydrochloride 12.0 g (73 mmol) of 2,6-dimethyl-4-hydroxy acetophenone and 17.6 g (146 mmol) of 2-tolualdehyde were dissolved in 150 ml of methanol, and 29 g of 50% strength sodium hydroxide solution (365 mmol) were added, and the mixture was refluxed for 2 h. It was left to stir at RT overnight and concentrated under reduced pressure. The residue was taken up in dilute hydrochloric acid and extracted with methylene chloride. The organic phase was dried and concentrated under reduced pressure. The product obtained in this way was recrystallized from petroleum ether. 14 g of 2',6'-dimethyl-4'-hydroxy-2-methylchalcone were obtained.

4.0 g (15 mmol) of the above product, 2.25 g (15 mmol) of N-(3-chloropropyl)diethylamine, 4.1 g (30 mmol) of potassium carbonate and 0.2 g of 18-crown-6 in 50 ml of ethyl methyl ketone were refluxed for 4 h. The carbonate was filtered off, and the filtrate was concentrated under reduced pressure. The residue was taken up in dilute hydrochloric acid and washed with ether. The aqueous phase was made alkaline with dilute sodium hydroxide solution and extracted with methylene chloride. The organic phase was dried and excess ethereal hydrogen chloride solution was added. 4.7 g of the product were obtained as the hydrochloride.

Melting point 162°–165° C.

The following were prepared in a manner similar to Example 21:

22. 2',6'-Dimethyl-4'-(3-(1-pyrrolidinyl)propoxy)-2-methylchalcone hydrochloride
 Melting point 217°–218° C.
23. 2',6'-Dimethyl-4'-(2-(1-piperidinyl)ethoxy)-2-methylchalcone hydrochloride
 Melting point 193°–194° C.
24. 3',4'-Dimethyl-4'-(2-(1-pyrrolidinyl)ethoxy)-4-methoxychalcone fumarate
 Melting point 185°–186° C.

EXAMPLE 25

3,5-Dimethyl-4-(2-(1-pyrrolidinyl)ethoxy)-3'-(2-tolyl)-propiophenone fumarate 8.75 g (110 mmol) of 3,,5,-dimethyl-4,-(2-(1-pyrrolidinyl)ethoxy)-2-methylchalcone tosylate were dissolved in 100 ml of methanol, 1 g of palladium/carbon (10% was added, and the mixture was hydrogenated until an equi-molar quantity of hydrogen had been absorbed. The catalyst was filtered off, and the filtrate was concentrated under reduced pressure. The product was treated with sodium hydroxide solution and precipitated with fumaric acid. 4.5 g of the abovementioned fumarate were obtained.

Melting point 108°–110° C.

The following were prepared in a manner similar to Example 25:

26. 2,6-Dimethyl-4-(2-(1-pyrrolidinyl)ethoxy)-3'-(2-tolyl)propiophenone hydrochloride
 Melting point 124°–126° C.
27. 3,5-Dimethyl-3'-(2-methoxyphenyl)-4-(2-(piperidinyl) ethoxy)propiophenone fumarate
 Melting point 121°–123° C.
28. 3,5-Dimethyl-4-(2-(1-piperidinyl)ethoxy)-3'-(2-tolyl)propiophenone fumarate
 Melting point 117°–120° C.
29. 4-(2-(1-Diethylamino)ethoxy)-3,5-dimethyl-3'-(2-tolyl)propiophenone fumarate
 Melting point 83'–86° C.
30. 3,5-Dimethyl-4-(3-(1-pyrrolidinyl)propoxy)-3'-(2-tolyl)propiophenone fumarate
 Melting point 186°–187° C.
31. 3,5-Dimethyl-3'-(2-ethylphenyl)-4-(2-(1-pyrrolidinyl)ethoxy)propiophenone fumarate
 Melting point 96°–98° C.
32. 3,5-Dimethyl-3'-(2-ethylphenyl)-4-(2-(1-piperidinyl)ethoxy)propiophenone fumarate
 Melting piont 126°–129° C.
33. 3,5-Dimethyl-3'-(2-methoxyphenyl)-4-(2-(1-pyrrolidinyl)ethoxy)propiophenone fumarate
 Melting point 102°–106° C.
34. 3,5-Dimethyl-3'-(4-methoxyphenyl)-4-(2-(1-pyrrolidinyl)ethoxy)propiophenone fumarate
 Melting point 135°–138° C.
35. 3,5-Dimethyl-3'-(4-methoxyphenyl)-4,2-(1-piperidinyl)ethoxy)propiophenone tosylate
 Melting point 125°–128° C.
36. 3,5-Dimethyl-3'-(4-methoxy-2-methylphenyl)-4-(2-(1-pyrrolidinyl)ethoxy)propiophenone hydrochloride
 Melting point 131°–136° C.

37. 3,5-Dimethyl-3'-(4-methoxy-2-methylphenyl-4-(2-(1-piperidinyl)ethoxy)propiophenone fumarate Oil

We claim:

1. A p-hydroxy phenone derivative of the formula I:

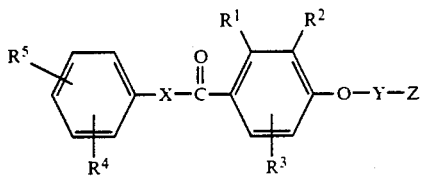

where $R^1$, $R^2$ and $R^3$ are identical or different and are methyl, chlorine, bromine or hydrogen, but $R^1$, $R^2$ and $R^3$ are not all H; $R^4$ and $R^5$ are identical or different and are H, $C_1$-$C_4$ alkyl, or $OR^6$, but $R^4$ and $R^5$ are not both H; X is a —CH=CH—, —CH$_2$CH$_2$— or —CH$_2$- bridge; Y is a straight-chain or branched, saturated or unsaturated $C_1$-$C_4$ bridge, and Z is $NR^6R^7$, where $R^6$ and $R^7$ are, independently of one another, $C_{1\text{-}4}$-alkyl, or Z is pyrrolidinyl, piperidinyl or morpholinyl, as well as the physiologically tolerated salts thereof.

2. A p-hydroxy phenone derivative as claimed in claim 1, wherein $R^1$ and $R^2$ and CH$_3$ groups in the 3,5 positions and $R^3$ is H.

3. A p-hydroxy phenone derivative of the formula I

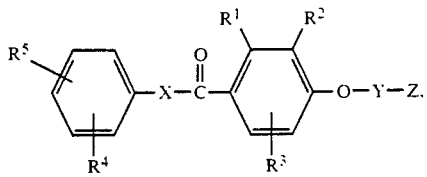

where
$R^1$, $R^2$ and $R^3$ are identical or different and are methyl, chlorine, bromine and hydrogen, but $R^1$, $R^2$ and $R^3$ are not all H, $R^4$ and $R^5$ are identical or different and are H, $C_1$-$C_4$-alkyl, or $OR^6$, but $R^4$ and $R^5$ are not both H, X is a —CH=CH—, —CH$_2$CH$_2$ or —CH$_2$— bridge, Y is a straight-chain or branched, saturated or unsaturated $C_1$-$C_4$ bridge, and Z is pyrrolidinyl, as well as the physiologically tolerated salts thereof.

4. A pharmaceutical formulation useful as an anti-arrhythmic of Vaughan-Williams class III, comprising, as the active ingredient, a pharmaceutically effective amount of the p-hydroxyphenone derivative of claim 1 in combination with pharmaceutically acceptable excipients.

5. The formulation of claim 4, wherein the amount of said p-hydroxy phenone derivative ranges from 0.001 to 1% by weight.

6. The pharmaceutical formulation of claim 4, wherein said composition, as a single dose, contains from 10 to 500 mg of said p-hydroxy phenone derivative.

7. The pharmaceutical formulation of claim 4, which is effective as an anti-arrhythmic of Vaughan-Williams Class III.

* * * * *